(12) United States Patent
Eilers et al.

(10) Patent No.: US 8,510,883 B2
(45) Date of Patent: Aug. 20, 2013

(54) METHOD OF POSITIONING A PATIENT FOR MEDICAL PROCEDURES

(75) Inventors: George J. Eilers, Evergreen, CO (US); J. David Stienmier, Denver, CO (US); Wes Weber, Golden, CO (US)

(73) Assignee: Arcscan, Inc., Morrison, CO (US)

( * ) Notice: Subject to any disclaimer, the term of this patent is extended or adjusted under 35 U.S.C. 154(b) by 151 days.

(21) Appl. No.: 12/754,444

(22) Filed: Apr. 5, 2010

(65) Prior Publication Data

US 2011/0099718 A1     May 5, 2011

Related U.S. Application Data

(60) Provisional application No. 61/256,739, filed on Oct. 30, 2009.

(51) Int. Cl.
*A47C 20/00*     (2006.01)

(52) U.S. Cl.
USPC ............... 5/637; 5/636; 5/601; 5/644; 5/654; 5/911; 5/913; 5/655.4

(58) Field of Classification Search
USPC ............ 5/636, 601, 637, 644, 654, 709, 911, 5/913, 702, 655.4
See application file for complete search history.

(56) References Cited

U.S. PATENT DOCUMENTS

| | | | |
|---|---|---|---|
| 3,371,660 A | 3/1968 | Benson | |
| 3,821,891 A | 7/1974 | Collins et al. | |
| 4,114,214 A * | 9/1978 | VonHeck | 297/284.1 |
| 4,183,249 A | 1/1980 | Anderson | |
| 4,206,763 A | 6/1980 | Pedersen | |
| 4,227,780 A | 10/1980 | Ohta et al. | |
| 4,245,250 A | 1/1981 | Tiemann | |
| 4,347,213 A * | 8/1982 | Rogers, Jr. | 264/510 |
| 4,484,569 A | 11/1984 | Driller et al. | |
| 4,550,607 A | 11/1985 | Maslak et al. | |

(Continued)

FOREIGN PATENT DOCUMENTS

| | | |
|---|---|---|
| CA | 2295431 | 7/2001 |
| CA | 2299483 | 7/2001 |

(Continued)

OTHER PUBLICATIONS

Binder, "SL-OCT and Ultrasound Support the Need for New Phakic IOL Sizing Strategies", Euro Times, Mar. 2007, p. 11.

(Continued)

*Primary Examiner* — Robert G Santos
*Assistant Examiner* — David E Sosnowski
(74) *Attorney, Agent, or Firm* — Sheridan Ross PC (57) ABSTRACT

A method and apparatus are disclosed for a method for securing a patient for a medical procedure and specifically for an innovative headrest system for securing a patient for an ocular imaging procedure. The approach avoids the need for linkages and sliding rods and such. Instead, it relies on three independently movable face rests (two for the forehead or temples and one for the chin) each with a deformable cushion that is urged into conformity with the patient's head and chin during an adjustment phase of operation. Once a comfortable position and suitable conforming shape is achieved, the positions of the face rests are rigidly fixed and the shape of the cushions are rendered rigid and non-deformable, by application of a light vacuum, for the procedural or imaging phase of operation.

11 Claims, 5 Drawing Sheets

(56) References Cited

U.S. PATENT DOCUMENTS

| | | | |
|---|---|---|---|
| 4,564,018 A | 1/1986 | Hutchison et al. | |
| 4,807,634 A | 2/1989 | Enjoji et al. | |
| 4,815,047 A | 3/1989 | Hart | |
| 4,817,432 A | 4/1989 | Wallace et al. | |
| 4,823,801 A | 4/1989 | Sakane | |
| 4,858,124 A | 8/1989 | Lizzi et al. | |
| 4,858,613 A | 8/1989 | Fry et al. | |
| 4,930,512 A | 6/1990 | Henriksen et al. | |
| 4,932,414 A | 6/1990 | Coleman et al. | |
| 5,029,587 A | 7/1991 | Baba et al. | |
| 5,079,786 A * | 1/1992 | Rojas | 5/654 |
| 5,103,517 A * | 4/1992 | Krouskop | 5/702 |
| 5,116,114 A | 5/1992 | Nakamura et al. | |
| 5,293,871 A | 3/1994 | Reinstein et al. | |
| 5,331,962 A | 7/1994 | Coleman et al. | |
| 5,369,454 A | 11/1994 | Reinstein et al. | |
| 5,387,180 A | 2/1995 | Lehmer | |
| 5,460,179 A | 10/1995 | Okunuki et al. | |
| 5,487,388 A | 1/1996 | Rello et al. | |
| 5,556,169 A * | 9/1996 | Parrish et al. | 297/452.28 |
| 5,614,099 A | 3/1997 | Hirose et al. | |
| 5,626,150 A * | 5/1997 | Johnson et al. | 5/628 |
| 5,626,594 A | 5/1997 | Smith | |
| 5,776,068 A | 7/1998 | Silverman et al. | |
| 5,826,583 A * | 10/1998 | Wood | 5/627 |
| 5,832,550 A * | 11/1998 | Hauger et al. | 5/621 |
| 5,855,207 A * | 1/1999 | Moenning et al. | 128/845 |
| 5,906,205 A * | 5/1999 | Hiebert | 128/845 |
| 5,966,763 A * | 10/1999 | Thomas et al. | 5/715 |
| 5,971,006 A * | 10/1999 | Seigerschmidt | 137/223 |
| 6,053,613 A | 4/2000 | Wei et al. | |
| 6,145,143 A * | 11/2000 | Hicks et al. | 5/722 |
| 6,154,204 A | 11/2000 | Thompson et al. | |
| 6,198,956 B1 | 3/2001 | Dunne | |
| 6,315,727 B1 | 11/2001 | Coleman et al. | |
| 6,374,439 B2 * | 4/2002 | Heimbrock et al. | 5/622 |
| 6,487,447 B1 | 11/2002 | Weimann et al. | |
| 6,491,637 B2 | 12/2002 | Foster et al. | |
| 6,514,099 B2 | 2/2003 | Endo | |
| 6,574,813 B2 * | 6/2003 | Bolden et al. | 5/689 |
| 6,629,929 B1 | 10/2003 | Jago et al. | |
| 6,837,855 B1 | 1/2005 | Puech | |
| 6,868,569 B2 * | 3/2005 | VanSteenburg | 5/709 |
| 6,887,203 B2 | 5/2005 | Phillips et al. | |
| 6,923,767 B2 | 8/2005 | Saied et al. | |
| 6,981,417 B1 | 1/2006 | Oravecz | |
| 7,048,690 B2 | 5/2006 | Coleman et al. | |
| 7,168,116 B2 * | 1/2007 | Reger et al. | 5/713 |
| 7,356,905 B2 | 4/2008 | Ketterling et al. | |
| 7,454,024 B2 | 11/2008 | Ketterling et al. | |
| 7,474,041 B2 | 1/2009 | Ketterling et al. | |
| 2003/0142269 A1 | 7/2003 | Cumming | |
| 2004/0220478 A1 | 11/2004 | Wallace et al. | |
| 2005/0120479 A1 * | 6/2005 | Habashi et al. | 5/610 |
| 2006/0029525 A1 | 2/2006 | Laugharn, Jr. et al. | |
| 2006/0241533 A1 | 10/2006 | Geller | |
| 2007/0083995 A1 * | 4/2007 | Purdy et al. | 5/702 |
| 2007/0239030 A1 | 10/2007 | Prager et al. | |
| 2007/0276233 A1 | 11/2007 | Besson et al. | |
| 2008/0097214 A1 | 4/2008 | Meyers et al. | |
| 2009/0192389 A1 | 7/2009 | Eilers et al. | |
| 2009/0234369 A1 | 9/2009 | Bax et al. | |
| 2010/0004537 A1 | 1/2010 | Eilers et al. | |
| 2010/0004538 A1 | 1/2010 | Eilers et al. | |
| 2010/0031448 A1 * | 2/2010 | Hijlkema | 5/702 |

FOREIGN PATENT DOCUMENTS

| | | |
|---|---|---|
| CA | 2395203 | 7/2001 |
| CA | 2409234 | 4/2004 |
| JP | 2006-149001 | 6/2006 |

OTHER PUBLICATIONS

U.S. Appl. No. 12/638,661, filed Dec. 15, 2009, Eilers et al.

Coleman et al., "Ultrasonography of the Eye and Orbit", Second Edition, published by Lippincott Williams & Wilkins, 2006, pp. 1-186.

Ketterling, "Design and Fabrication of a 40-MHz Annular Array Transducer", IEEE Transactions on Ultrasonics, Ferroelectrics, and Frequency Control, Apr. 2005, vol. 52, No. 4, pp. 672-681.

Ketterling, "Operational Verification of a 40-MHz Annular Array Transducer", IEEE Transactions on Ultrasonics, Ferroelectrics, and Frequency Control, Mar. 2006, vol. 53, No. 3, pp. 623-630.

Mamou, "Chirp-Coded Excitation Imaging With a High-Frequency Ultrasound Annular Array", IEEE Transactions on Ultrasonics, Ferroelectrics, and Frequency Control, Feb. 2008, vol. 55, No. 2.

Pinero et al., "Equivalence, Differences Identified in Biometric Analysis", Cataract & Refractive Surgery Today, Mar. 2008, vol. 3, No. 12, pp. 46-49.

Reinstein, "Subsurface Screening for Keratoconus—Accurate Measurements of the Epithelial and Stromal Layers Aid in Diagnosis", Cataract and Refractive Surgery Today, May 2007, pp. 88-89.

Roholt, "Sizing the Visian ICL", Cataract and Refractive Surgery Today, May 2007, p. 50.

Silverman et al., "Improved System for Sonographic Imaging and Biometry of the Cornea", J. Ultrasound Med., 1997, vol. 16, pp.

Background of the Invention for the above-captioned application filed Apr. 5, 2010.

\* cited by examiner

METHOD OF POSITIONING A PATIENT FOR MEDICAL PROCEDURES

CROSS REFERENCE TO RELATED APPLICATION

The present application claims the benefits, under 35 U.S.C. §119(e), of U.S. Provisional Application Ser. No. 61/256,739 entitled "Method of Positioning a Patient for Medical Procedures", filed Oct. 30, 2009 which is incorporated herein by this reference.

FIELD

The present invention relates in general to a method for securing a patient for a medical procedure and specifically for an innovative headrest system for securing a patient for an optical imaging procedure.

BACKGROUND

Many optical instruments, especially those used in ophthalmology, require fixation of a person's head relative to the optical and mechanical structure of the instrument. A commonly used approach is to provide one or more surfaces against which the patient rests his forehead and chin (see FIG. 1 for example). Given the relatively large and unpredictable variability in the shape of heads and chins, this presents a challenge to the designer. The designer must provide adjustable positions for the surfaces that can be set for each patient and then locked to prevent further movement. This is conventionally done by including linkages and sliding rods with lever or screw operated brakes.

SUMMARY

These and other needs are addressed by the present invention. The various embodiments and configurations of the present invention are directed generally to a method for securing a patient for a medical procedure and specifically for an innovative headrest system for securing a patient for an ocular imaging procedure.

The present invention avoids or greatly reduces the need for linkages and sliding rods and such. Instead, it relies on three independently movable face rests (two for the forehead or temples and one for the chin) each with a deformable cushion that is urged into conformity with the patient's head and chin during an adjustment phase of operation. Once a comfortable position and suitable conforming shape is achieved, the positions of the face rests are rigidly fixed and the shape of the cushions are rendered rigid and non-deformable, by application of a light vacuum, for a procedural or imaging phase of operation.

Suitable cushions can be constructed by filling a flexible, gas-impermeable containing bag with a granular material. The bag may be constructed, for example, of a rubber membrane, or alternatively, by a rubber-coated fabric. The granular material may be any granular solid that is fine enough to render its granular composition imperceptible through the surface of the cushion. Suitable materials are, for example, glass beads, plastic beads, sand or the like. The particle size may be in the range from about 50 microns to about 3 mm in diameter, and particle sizes may vary within the cushion.

During the adjustment phase, three separate face rests (one chin rest and two temple rests) are moved into approximate position to position the patient's head while allowing the operator a clear line of vision to the patient's eye. The cushions, which are initially deformable during the adjustment phase, are maintained close the ambient atmospheric pressure so that there is little pressure differential between the inside and outside of the cushion. With differential pressures in the range from about −0.01 atmosphere to about +0.03 atmosphere, the cushion is easily deformed when the patient places his head or chin firmly in contact with the cushion. This causes the cushion to conform to the head in such a way as to allow small adjustments of the head position to permit alignment with sealing devices or optical components.

When the head is aligned and the patient is comfortable, the chamber between the bottom of the face rests and the device and the insides of the cushions are pumped to a lower pressure in the range of about −0.5 to about −0.9 atmosphere for the procedural phase, causing atmospheric pressure to both clamp the face rests in place and force the cushions' coverings to press firmly against the contained granular material. This locks face rests in place and locks the granular material into place, maintaining the outer form of the cushion against subsequent head movements and holding the head rigidly in the desired position and alignment.

Lowering the pressure to lock the face rests and cushions may be done manually by a hand pump, or by computer control using a mouse or voice control.

The following definitions are used herein:

An ultrasound scanner is an ultrasound scanning device utilizing a transducer that both sends and receives pulses as it moves in a prescribed manner along one or more guide tracks, which guide tracks allow the transducer to be aimed in order to scan features of differing acoustic impedances.

An arc scanner is an ultrasound scanning device utilizing a transducer that both sends and receives pulses as it moves along an arcuate guide track, which guide track has a center of curvature whose position can be moved to scan curved surfaces of differing acoustic impedances.

Auto-centering means automatically, typically under computer control, causing centration of the arc scanning or ultrasonic scanning transducer with the eye component of interest.

Fixation means having the patient focus an eye on an optical target such that the eye's optical axis is in a known spatial relationship with the optical target. In fixation, the light source is axially aligned in the arc plane with the light source in the center of the arc so as to obtain maximum signal strength such that moving away from the center of the arc in either direction results in signal strength diminishing equally in either direction away from the center.

An intraocular lens is an artificial lens that is implanted in the eye to take the place of the natural lens.

LASIK is a procedure performed on the cornea for correcting refractive errors, such as myopia, hyperopia, and astigmatism. Commonly, an excimer laser selectively removes tissue from the inside of the cornea, after exposing it by cutting a thin flap, so as to reshape the external shape of the cornea.

Ocular means having to do with the eye or eyeball.

Ophthalmology means the branch of medicine that deals with the eye.

Optical as used herein refers to processes that use light rays.

Phakic intraocular lenses, or phakic lenses, are lenses made of plastic or silicone that are implanted into the eye permanently to reduce a person's need for glasses or contact lenses. Phakic refers to the fact that the lens is implanted into the eye without removing the eye's natural lens. During phakic lens implantation surgery, a small incision is normally made in the front of the eye. The phakic lens is inserted through the incision and placed just in front of or just behind the iris.

Presbyiopia is typically caused by a loss of elasticity of the natural lens inside the eye. This occurs as part of the ageing process and, although it cannot be 'cured', it can be corrected by wearing glasses or implanting an artificial lens.

Refractive means anything pertaining to the focusing of light rays by the various components of the eye.

Sector scanner is typically a hand-held ultrasonic scanner that sweeps a sector like a radar. The swept area is pie-shaped with its central point typically located near the face of the ultrasound transducer.

Ultrasonic or ultrasound means sound that is above the human ear's upper frequency limit. When used for imaging an object like the eye, the sound passes through a liquid medium, and its frequency is many orders of magnitude greater than can be detected by the human ear. For high-resolution acoustic imaging in the eye, the frequency is typically in the approximate range of about 5 to about 80 MHz.

The visual axis of the eye is the line joining the object of interest and the fovea and which passes through the nodal points.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

DETAILED DESCRIPTION

The present invention is a method applicable for securing a patient for application of a medical procedure. The preferred method relies on movable face rests and deformable cushions that are independently urged into conformity with the patient's body feature of interest during an adjustment phase of operation. Once a comfortable position and suitable conforming shape is achieved, the face rests are rendered rigid and unmovable while the cushions rendered rigid and non-deformable during a procedural phase of operation. Specifically, the present invention is illustrated with an innovative headrest for an ocular imaging procedure wherein the method relies on movable face rests and deformable cushions that are urged into conformity with the patient's forehead and chin.

The present invention is illustrated for an ultrasonic arc scanning instrument but, as can be appreciated, the invention can be applied to other diagnostic devices including optical scanning devices.

Prior Art Headrests

Figure 1A:
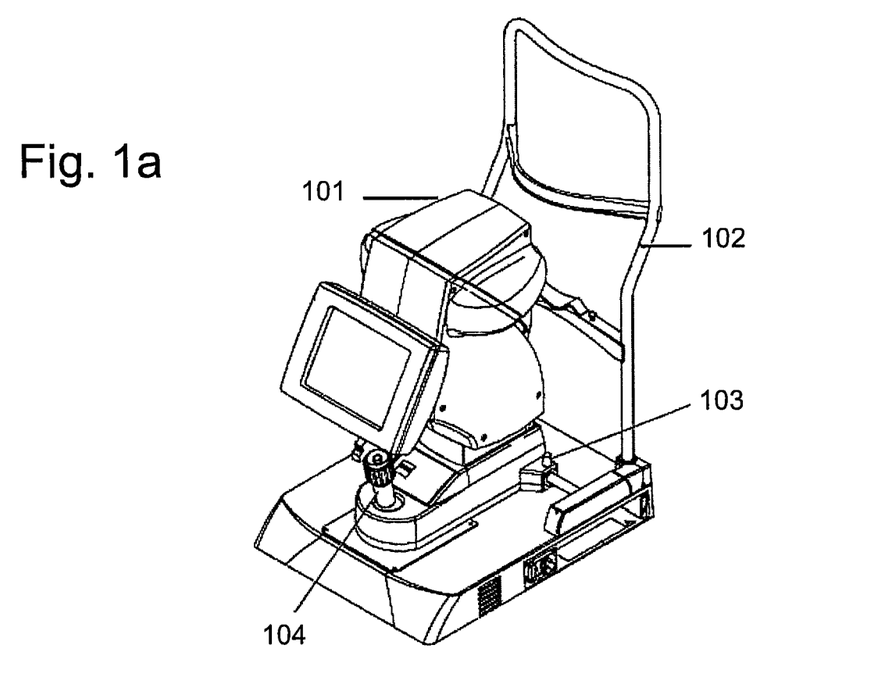
FIG. 1 shows a prior art headrest apparatus.
Figure 1B:
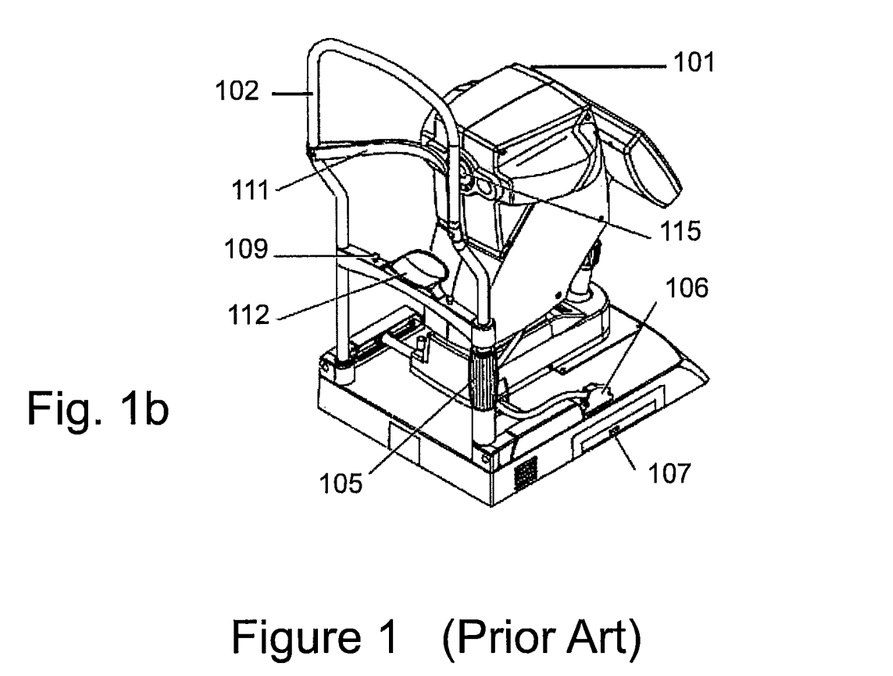

FIG. 1 shows a typical prior art head rest apparatus. A typical imaging device 101 for measuring features in an eye is shown from two different angles in FIGS. 1a and 1b. The imaging eyepiece 115 is shown in FIG. 1b for reference. Securing the patient's head relative to the imaging device 101 is conventionally done by a headrest assembly 102 which typically includes a forehead rest 111 and a chin rest 112. The headrest assembly 102 is typically adjusted by mechanical linkages 106; sliding rods 103; and lever or screw operated brakes 104, 105 and 109. The present invention avoids or greatly reduces the need for such linkages and sliding rods and such.

A prior art arc scanner known as the Artemis 2 is described in Reference 1, "Sizing the Visian ICL", Philip C. Roholt, M.D., Cataract and Refractive Surgery Today, May 2007. The patient looks downward at approximately 45 degrees from horizontal. The patient's head is positioned by a fixed chin rest and two fixed forehead rests which are adjusted mechanically to best position the patient's head.

Prior Art Ultrasonic Scanning

There are two different types of scanning strategies for ultrasonic scanners capable of imaging most regions of the interior of an eye. The so-called arc scanner is used for generating a comprehensive ultrasonic image of various regions of an eye including the entire interior of an eye or generating a comprehensive ultrasonic image of a desired component within an eye. In this type of scanner, which is described, for example, in U.S. Pat. Nos. 6,315,727, 6,491,637, 6,887,203 and 7,048,690, a transducer is moved in an arc whose center is set at a location of interest in the eye.

A sector scanner is also capable of producing an ultrasonic image of a particular location with an eye. In this type of scanner, which is described, for example, in U.S. Pat. Nos. 4,245,250, 4,817,432, 5,029,587 and 5,331,962, an ultrasonic transducer is held in the operator's hand while pressed against a patient's eye and is then caused to rotate about a fixed position so as to produce an image in a localized region of interest within the eye.

In both the arc and sector ultrasonic scanners, the transducer acts as both the transmitter and receiver of acoustic signals. This technique is described, for example, in U.S. Pat. No. 5,293,871. The transducer emits a short acoustic pulse and then receives the reflected acoustic signal.

A sector scanner can be used to measure the thickness of an eye component such as, for example, the thickness of the cornea or the thickness of the lens. A sector scanner cannot be used to measure the width of specular features that extend laterally, such as, for example, the length of a LASIK scar, because only that small portion of the cornea that is perpendicular to the acoustic beam and reflects acoustic energy back to the transducer is visible to a sector scanner. Because a sector scanner is a hand-held device, it cannot practically make an accurate quantitative measurement of an eye component.

An arc scanner, on the other hand, can be used to accurately and precisely measure the thickness of an eye component such as, for example, the thickness of the cornea or the thickness of a lens as well as to measure the length of specular features that extend laterally, such as, for example, the length of a LASIK scar or the lateral length of a natural or implanted lens. Because an arc scanner precisely positions and moves its transducer with respect to a patient's eye, it is capable of generating a quantitative measurement of an eye component or a quantitative measurement of substantially all of the interior regions of an eye. As such, it can be appreciated that an arc scanner would require a headrest system capable of fixing a patient's head comfortably with respect to the scan head of the arc scanner as a precondition of obtaining an accurate measurement of an eye component or of substantially all of the interior regions of an eye.

An ultrasound scanner is an ultrasound scanning device utilizing a transducer that both sends and receives pulses as it moves in a prescribed manner along one or more guide tracks and is therefore a more general imaging device than a traditional arc scanner.

Both the arc scanner and the more general ultrasound scanner require a continuous path for the transmitted and reflected ultrasonic pulses between the transducer and the patient's eye. The transducer and its guide track assemblies are immersed in a chamber of water to provide a continuous transmission path for the acoustic signals. The patient's eye must also be immersed in water to provide continuity of the transmission path for the acoustic signal. The latter is accomplished by use of a disposable eyepiece which includes a hygienic barrier which separates the water chamber in which the transducer and guide track assemblies are contained from the water in which the patients eye is immersed.

Various configurations of an arc scanning device are described in U.S. patent application Ser. No. 12/347,674, entitled "Components for an Ultrasonic Arc Scanning Apparatus", filed Dec. 31, 2008 and U.S. patent application Ser. No. 12/418,392 entitled "Procedures for an Ultrasonic Arc Scanning Apparatus" filed Apr. 3, 2009, both of which are incorporated herein by reference. A multi-track ultrasound scanner is described in U.S. patent application Ser. No. 12/638,661 entitled "Alignment and Imaging of an Eye with an Ultrasonic Scanner", filed Mar. 9, 2010, which is also incorporated herein by reference.

Figure 2:
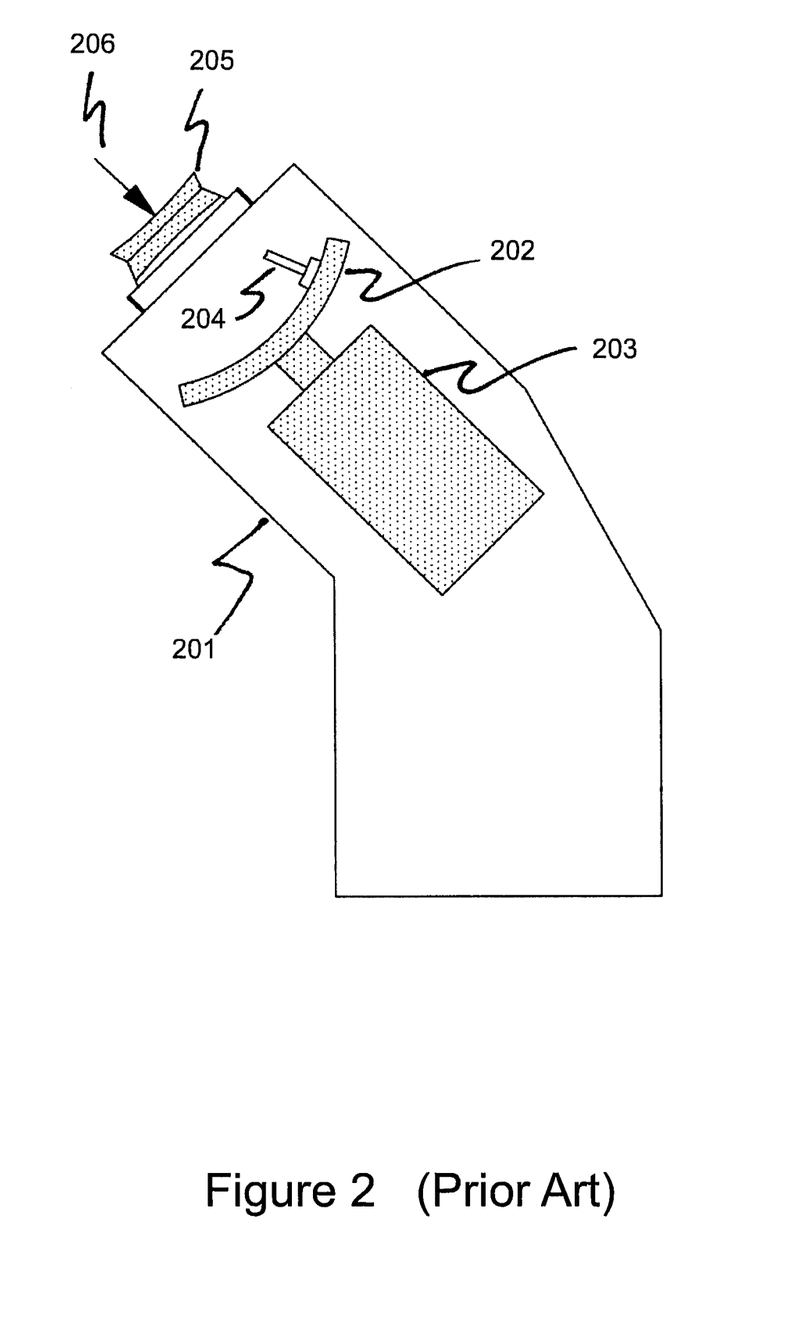
FIG. 2 is a schematic representation of an ultrasound or arc scanning apparatus which is prior art.

FIG. 2 is a schematic representation of an arc scanning apparatus which is prior art. The arc scanning apparatus of this example is comprised of an arc scanning machine 201 which includes a scan head 202 (shown here as an arcuate guide with transducer 204 on a transducer carriage which moves back and forth along the arcuate guide track), an ultrasonic transducer 204 and a disposable eyepiece 205. The arc scanning machine 201 is typically connected to a computer (not shown) which includes a processor module, a memory module, and a video monitor. The patient is seated at the machine 201 with their eye engaged with disposable eyepiece 205 such as described in FIG. 3. The patient is fixed with respect to the scanning machine 201 by a headrest system (not shown) which is the subject of the present invention. The patient's eye component to be imaged is represented by input 221. The operator using mouse and/or keyboard and video screen inputs information into the computer selecting the type of scan and scan configurations as well as the desired type of output analyses. The operator, using mouse and/or keyboard, a video camera in scanning machine and video screen, then centers a set of cross hairs displayed on video screen on the desired component of the patient's eye, also displayed on video screen, setting one of the cross hairs as the prime meridian for scanning. Once this is accomplished, the operator instructs computer using either mouse and/or keyboard to proceed with the scanning sequence. Now the computer processor takes over the procedure and issues instructions to the scan head positioning mechanism 203, the scan head 202 and the transducer 204 and receives positional and imaging data. The computer processor proceeds with a sequence of operations such as for example: (1) rough focus transducer 204 on the selected eye component; (2) accurately center arc track with respect to the selected eye component; (3) accurately focus transducer 204 on the selected feature of the selected eye component; (4) rotate the arc track through a substantial angle and repeat steps (1) through (3) on a second meridian; (5) rotate the arc track back to the prime meridian; (6) initiate a set of A-scans along each of the of selected scan meridians, storing this information in the memory module; (7) utilizing the processor, converting the A-scans for each meridian into a set of B-scans and then processing the B-scans to form an image associated with each meridian; (8) performing the selected analyses on the A-scans, B-scans and images associated with each or all of the meridians scanned; and (9) outputting the data in a preselected format to an output device such as a printer. As can be appreciated, the patient's head must remain fixed with respect to the scanning machine 201 during the above operations, which in a modern arc or ultrasound scanning machine, can take several minutes.

Eyepiece

An eyepiece serves to complete a continuous acoustic path for ultrasonic scanning, that path extending in water from the transducer to the surface of the patient's eye. The eyepiece also separates the water in which the patient's eye is immersed from the water in the chamber in which the transducer guide track assemblies are contained. Finally, the eyepiece provides an additional steady rest for the patient and helps the patient to remain steady during a scan procedure.

Figure 3:
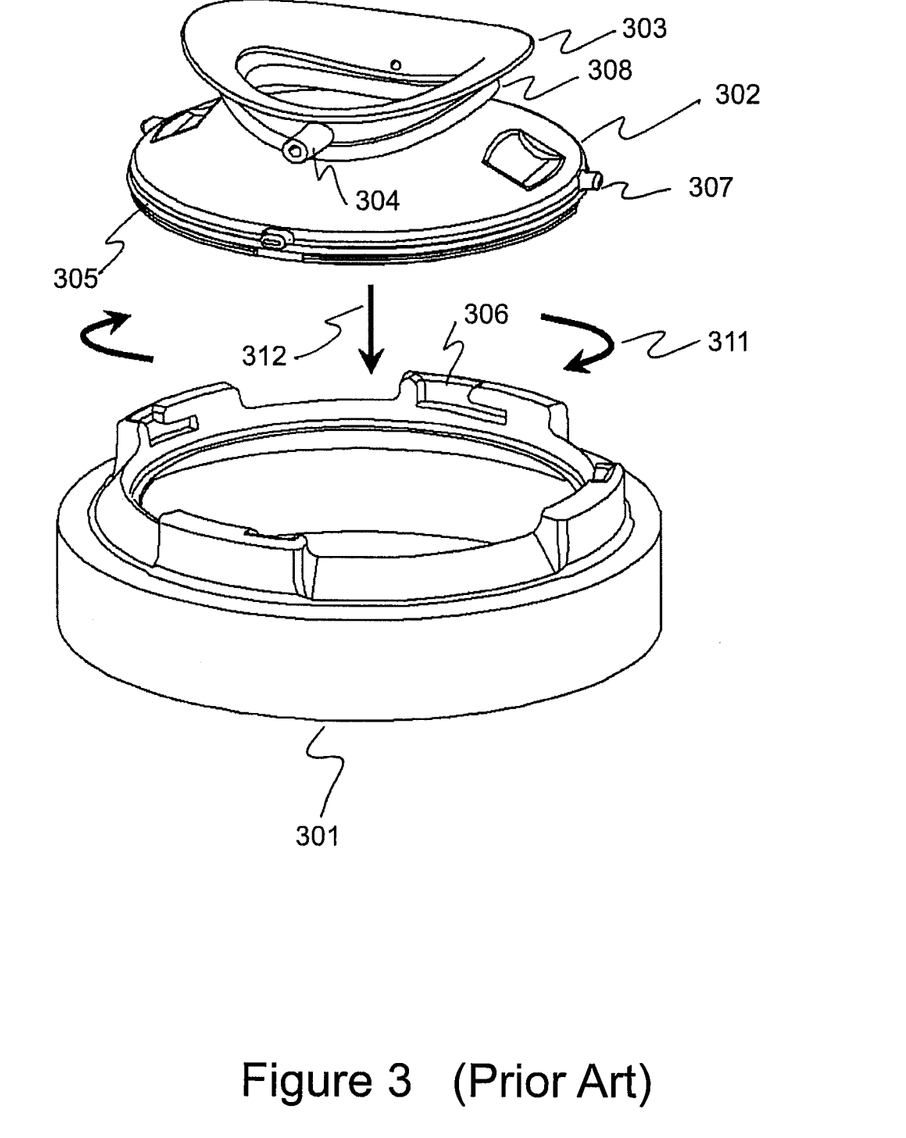
FIG. 3 illustrates an embodiment of an eyepiece for an ultrasound or arc scanner.

FIG. 3 illustrates an embodiment of an eyepiece that satisfies these requirements. The eyepiece consists of a mounting ring 301 and an eye seal ring 302. The mounting ring 301 is attached to and is typically a permanent part of the main scanner assembly. As shown here the mounting ring 301 has several attachment grooves 306 which can accept attaching mechanisms 307 on the eye seal ring 302. In this embodiment, the attaching mechanisms 307 are pushed down 312 into the attachment grooves 306 and then rotated 311 into position to form a mechanical connection that seals the eye seal ring 302 against the mounting ring 301 to prevent water leakage. This is also known as a bayonet type connection. There may be a sealing ring 305 which is compressed as the attaching mechanisms 307 are rotated 311 into position. The eye seal ring 302 has a soft rubber or foam contoured face seal 303 which is designed to seal against a typical human face around the eye that is to be scanned. The eye seal ring 302 is also shown with its water fill tube 304 on the top and a water drain tube 314 on the bottom. A sealed hygienic barrier (not shown) is formed as part of the eye seal ring 302 during manufacture and is typically located where the contoured face seal 303 is connected at location 308 to the main body of the eye seal ring 302.

The hygienic barrier or membrane may be permeable or semi-permeable to water as long as it is impermeable to bacteria, viruses, fungi, and other potentially harmful biological and chemical impurities. The membrane is preferably impermeable to water to provide superior isolation from biological and non-biological impurities that may be dissolved or carried in water. The membrane is preferably optically clear to allow a video camera to view the eye through the membrane. The membrane preferably passes acoustic pulses without significant energy absorption or reflection. These conditions can be substantially met by a membrane that is thinner than an acoustic pulse wavelength which is about 150 microns at 10 MHz and about 20 microns at 80 MHz.

A First Configuration of the Present Invention

Figure 4:
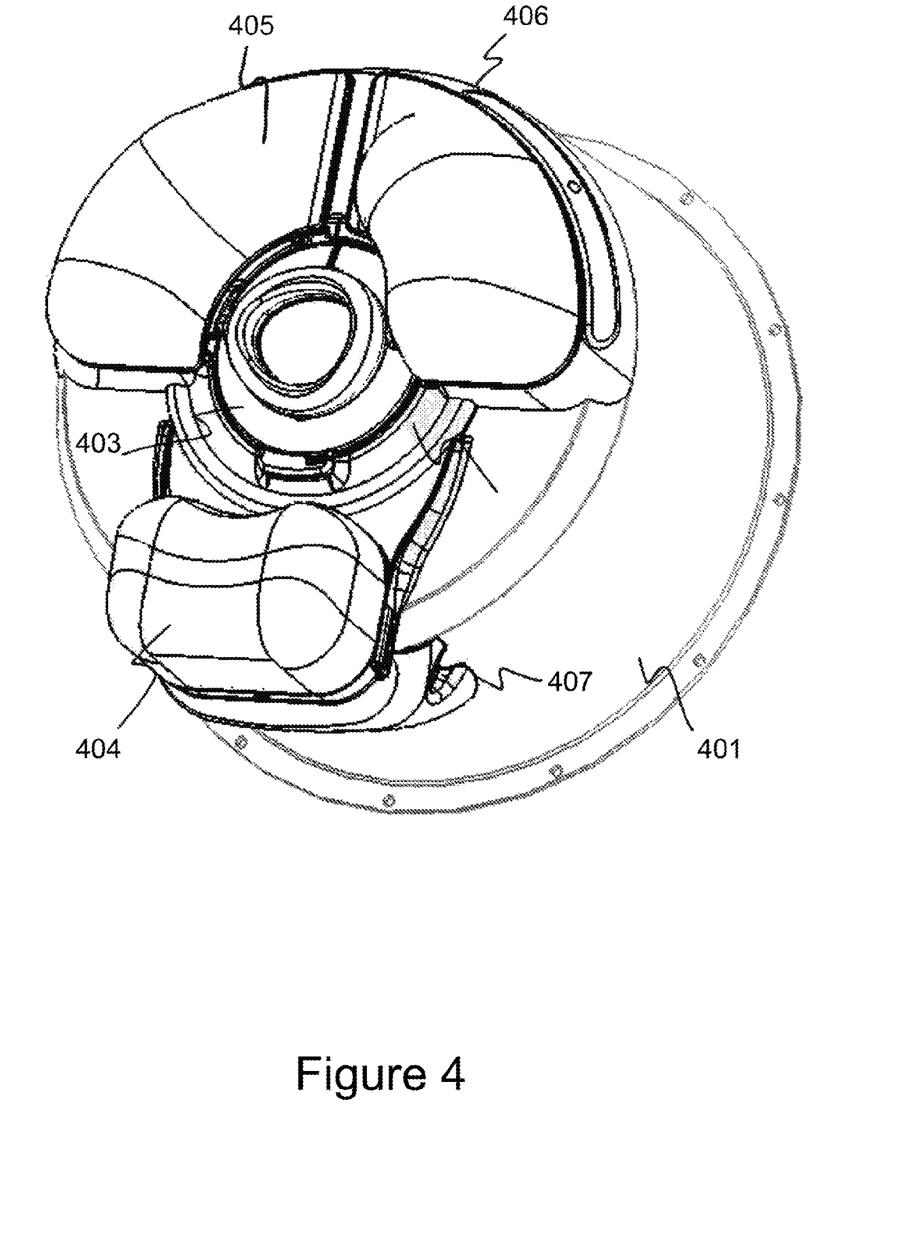
FIG. 4 is a schematic representation of a headrest of the present invention.

FIG. 4 is a schematic representation of a first configuration of a headrest of the present invention. FIG. 4 shows the body of an arc scan imaging device 401. The disposable eyepiece 403 is shown attached to an eyepiece retaining ring 402 which is permanently attached to the body of an arc scan imaging device 401. A headrest assembly is shown comprising a chin rest 404 and a two-piece forehead rest with left forehead rest section 405 and right forehead rest section 406. As can be appreciated, the headrest can be made of one piece rather than two. The head rest system also includes a detachable water collector 407 typically mounted under chin rest 404. The water collector 407 may be attached to the scanner body 401 in a variety of ways but preferably by magnetic attachment. The chin rest 404 is contoured such that water flows around the chin rest and into the water collector 407 in the event that water leaks from the eyepiece or in the event that water flows from the eyepiece if the patient pulls away prematurely when the eyepiece is full of water (the eyepiece is normally drained after the scanning procedure is completed). The flow path can be formed by shallow grooves or guides molded or otherwise affixed to the arc scanner body. When water flow ceases, the water collector 407 can be detached and emptied.

The cushions 404, 405 and 406 can be constructed by filling a flexible, gas-impermeable containing bag or capsule with a granular material. The bag or capsule may be constructed, for example, of a rubber membrane, or alternatively, by a rubber-coated fabric. The granular material may be any granular solid that is fine enough to render its granular composition imperceptible through the surface of the cushion. Suitable materials are, for example, glass beads, metal beads, plastic beads, sand or the like. The particle size may be in the range of about 50 microns to about 3 mm in diameter, and particle sizes may vary within the cushions. The granular material may also be made from suitable combinations of glass beads, metal beads, plastic beads, sand or the like.

During the adjustment phase, the cushions are maintained close the ambient atmospheric pressure so that there is little pressure differential between the inside and outside of the cushions. With differential pressures in the range from about 31 0.01 atmosphere (−0.147 psi) to about +0.03 atmosphere (+0.441 psi), the cushion is easily deformed when the patient places his or her head or chin firmly in contact with it. This causes the cushion to conform to the head in such a way as to allow small adjustments of the head position to permit alignment with sealing devices or imaging components. For example, in the illustration of the ultrasonic scanner, the patient must make small adjustments to align his or her eye with a scanning reference beam while also maintaining a seal between his or her face and a flexible eyepiece.

When the head is aligned and the patient is comfortable, the insides of the cushions are pumped to a lower pressure in the range of about −0.5 atmosphere (−07.35 psi) to about −0.9 atmosphere (−13.2 psi), causing atmospheric pressure to force the cushions' coverings to press firmly against the contained granular material. This locks the granular material into place, maintaining the outer form of the cushion against subsequent movements of the head and holding the head rigidly in the desired position and alignment for the procedural phase of operation.

It may be preferable for the granular material that is used to be constrained to keep within a desired size range and be absent of any fines. This would, for example, prevent clogging of vacuum pumps and eliminate a requirement for high performance filters.

It is also possible to include some liquids or gels in the spaces between the granular material in order to provide some lubrication. This may make it easier for the cushion to conform to the patient before a partial vacuum is drawn to lock in the desired contour of the cushions.

The cushions may be covered with a disposable paper, plastic or other covering to protect the cushions from patient's perspiration etcetera and to protect the patient from other patient's perspiration etcetera.

It may also be desirable to have a simple up/down mechanical adjustment for the chin rest to accommodate the large variation in patient head sizes. This could be a screw type adjustment of a spring loaded adjuster that locks when the pressure in the chin cushion is reduced to lock the granular chin cushion filler material into place.

Lowering the pressure to lock the cushions may be done manually by a hand pump, or by computer control using a mouse or voice control.

Tests with this prototype headrest showed that a patient could move his or her head until it was in a desired position while the bags were at ambient pressure. When a partial vacuum was created in the bags, the patient could no longer easily move his or her head relative to the imaging machine. This allows the patient to remain fixed relative to the imaging device for several minutes, enough time for several images of the eye to be made. This is especially useful for an arc scanning device which requires the patient to remain still while his or her eye is open and in contact with water which forms the transmission medium for acoustic imaging.

A number of variations and modifications of the invention can be used. As will be appreciated, it would be possible to provide for some features of the invention without providing others. For example, instead of using air pressure to lock the particles into place, magnetic force can be used. Either a dry powder or a slurry of ferrite particles could be substituted for the glass beads. With no magnetic field, the particles move fluidly. Applying either an AC or DC magnetic field in the range of about 0.1 tesla to about 0.7 tesla, the particles will lock into place.

A problem with this first configuration is that the cushions are large and can obstruct the scanner operator's view of the patients eye when the patient is in position with the cushions locked in place. In some cases, the scanner operator would prefer to remove one or more of the cushions for patient's who are having a problem getting comfortable with the eyepiece. A preferred embodiment of the headrest invention described in the following FIG. 5 overcomes these problems.

A Preferred Configuration of the Present Invention

Figure 5:
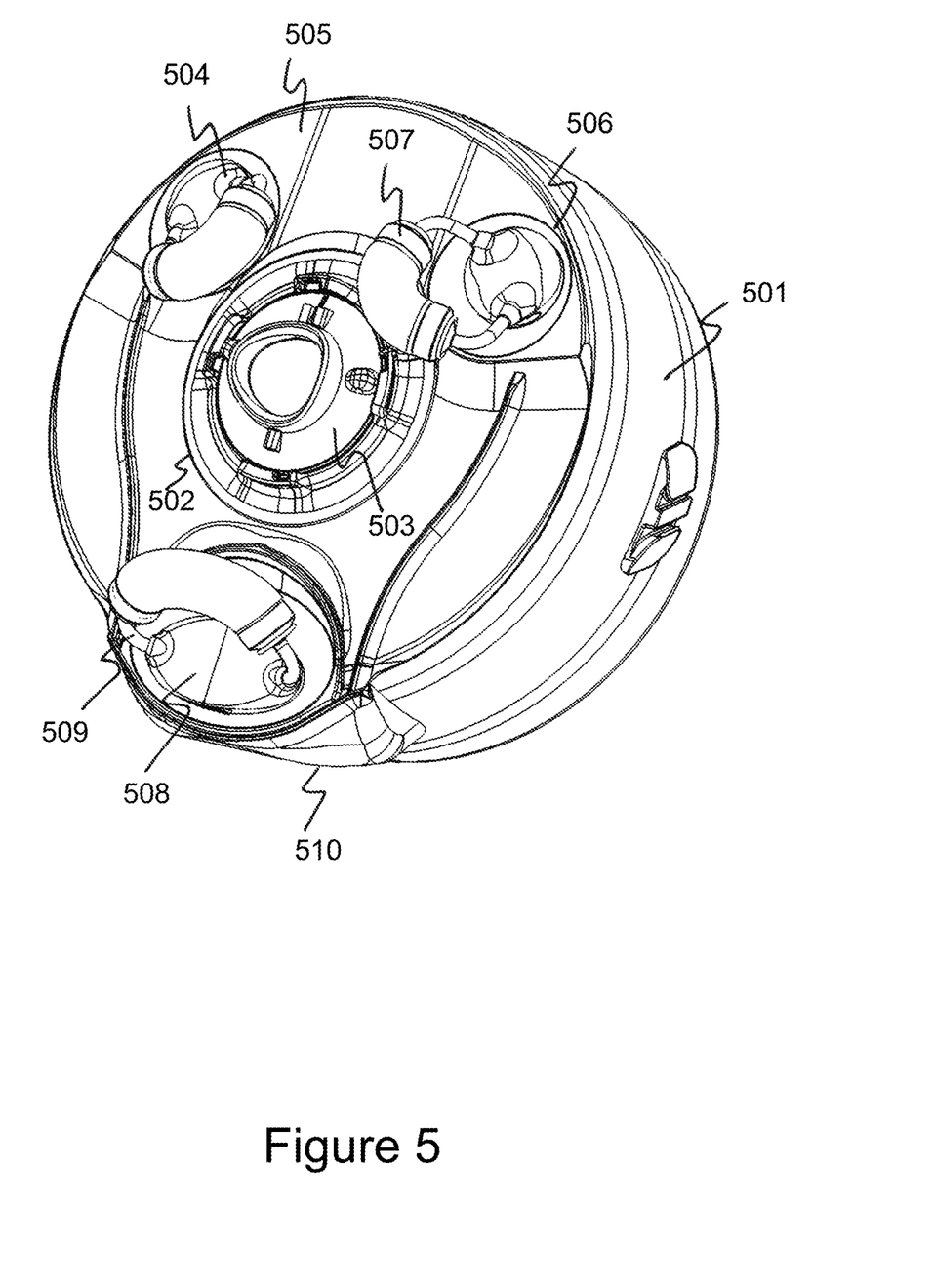
FIG. 5 is a schematic representation of a preferred embodiment of a headrest of the present invention.

FIG. 5 is a schematic representation of a preferred embodiment of a headrest system of the present invention. FIG. 5 shows the body of an imaging device 501. The disposable eyepiece 503 is shown attached to an eyepiece retaining ring 502 which is permanently attached to the body of the imaging device 501. A headrest system is shown comprising a chin rest 508 and a two temple or forehead rests 504 and 506. The head rest system also includes an independently detachable water collector 510. The water collector 510 may be attached to the body of the imaging device 501 in a variety of ways but preferably by magnetic attachment. Each of the chin rest 508 and two forehead rests 504 and 506 are comprised of a base plate such as 508, two connecting arms such as 509 and a central cushion such as 507. The base plate, connecting arms and central cushion form face rest subassemblies. The base plate of each face rest subassembly can be moved around on a metallic surface 505 which is on the front of the body of the imaging device 501. The underside of each base plate includes a magnet (not shown) which maintains the base plate in contact with the metallic surface such that the face rest subassembly can be readily positioned anywhere on its corresponding metallic surface 505. The underside of each base plate also includes an O-ring (not shown) that forms a light vacuum seal around the periphery of the underside of the base plate, thereby forming a seal around most of the underside of the base plate. In the center of the underside of each base plate, there is an orifice that connects a vacuum pathway that goes up through one or both of the arms of the face rest subassembly to the interior of the cushion of the face rest subassembly. When a light vacuum is applied, the face rest subassembly is locked onto the metallic surface and the cushion becomes rigid. As with the first headrest configuration, the cushions may be constructed by filling a flexible, gas-impermeable containing bag or capsule with a granular material.

The light vacuum is achieved by a small vacuum pump (not shown) which is connected via vacuum tubing to a small surge plenum. There are three separate vacuum lines from the surge plenum, one to each of the face rest subassemblies. Each of the three separate vacuum lines is to an orifice in the center of each of the three metallic surfaces on the face of the body of the imaging device 501. Each of the three separate vacuum lines has a check valve that is open when a vacuum is being pulled but will close when exposed to atmospheric air. Each face rest subassembly has a small button that, when depressed, releases the vacuum under the base plate so that face rest subassembly can be moved while the other two face rest subassemblies remain under vacuum and hence remain fixed. This temporary vacuum release is made possible by the check valves in the vacuum lines. As can be appreciated, when there is no vacuum, any or all of the face rest subassemblies can be removed by pulling up with enough force to overcome the magnetic attachment. When a face rest subassembly is removed, its vacuum connection is manually or, preferably, automatically closed off, thereby allowing the remaining face rest subassemblies to remain active.

During the adjustment phase, the face rest subassemblies are moved around to best fit the patient's temples and chin. During this time, the cushions are maintained close the ambient atmospheric pressure so that there is little pressure differential between the inside and outside of the cushions. With differential pressures in the range from about −0.01 atmosphere (−0.147 psi) to about +0.03 atmosphere (+0.441 psi), the cushion is easily deformed when the patient places his or her head or chin firmly in contact with it. This causes the cushions of each face rest subassembly to conform to the temples and chin in such a way as to allow small adjustments of the head position to permit alignment with sealing devices or imaging components. For example, in the illustration of the ultrasonic scanner, the patient must make small adjustments to align his or her eye with a scanning reference beam while also maintaining a seal between his or her face and a flexible eyepiece.

When the head is aligned and the patient is comfortable, the vacuum system is pumped to a lower pressure in the range of about −0.5 atmosphere (−7.35 psi) to about −0.9 atmosphere (−13.2 psi), causing atmospheric pressure to force the face rest subassemblies into rigid contact with their corresponding metallic surfaces and to force the cushions' coverings to press firmly against the contained granular material. This simultaneously locks each face rest subassembly in place and locks the granular material in each cushion into place, maintaining the outer form of the cushion against subsequent movements of the head and holding the head rigidly in the desired position and alignment.

The granular material inside the cushions may be any granular solid that is fine enough to render its granular composition imperceptible through the surface of the cushion. Suitable materials are, for example, glass beads, metal beads, plastic beads, sand or the like. The particle size may be in the range of about 50 microns to about 3 mm in diameter, and particle sizes may vary within the cushions. The granular material may also be made from suitable combinations of glass beads, metal beads, plastic beads, sand or the like.

It may be preferable for the granular material that is used to be constrained to keep within a desired size range and be absent of any fines. This would, for example, prevent clogging of vacuum pumps and eliminate a requirement for high performance filters.

It is also possible to include some liquids or gels in the spaces between the granular material in order to provide some lubrication. This may make it easier for the cushion to conform to the patient before a partial vacuum is drawn to lock in the desired contour of the cushions.

The cushions may be covered with a disposable paper, plastic or other covering to protect the cushions from patient's perspiration etcetera and to protect the patient from other patient's perspiration etcetera.

An advantage of this preferred embodiment is that each face rest subassembly is independently movable and the entire headrest system can be locked tight once the patient is in a comfortable position with respect to the scanner and with their eye properly positioned in the eyepiece. Another advantage of this preferred embodiment is the face rest subassemblies have a relatively low profile and this allows the operator to see around the cushions to determine if the patient is properly positioned and to see any problems that the patient may be having with the seal between their face and the eyepiece. Another advantage of this preferred embodiment is that any one of the face rest subassemblies may be removed if the operator deems this necessary.

Additional Applications

The principle of a cushion that can readily conform to a body component and then be made rigid by reversibly changing the state of the material in the cushion can be applied to other medical procedures as well as to non medical applications.

Patient's bodies or body parts often must be immobilized for medical procedures. Examples of such procedures are:
- radiation oncology where the patient must remain stationary for several minutes while a radiation beam is directed at a desired target on or within the body
- robotic surgery such as prostate surgery where the patient must remain immobile relative to the robotic surgical device for extended periods of time.
- medical scans such as for example an acoustic heart scan where a patient must remain immobile for extended periods of time (several minutes) then released and moved to another position where again the patient must remain immobile for another extended period of time and so on This invention can be applied to casts or neck braces for example where it is advantageous for the cast to be removed periodically. This can be done by removing the partial vacuum when it is desired to remove the cast or brace for a short period of time and then have the capability to readily re-apply the cast of brace simply by re-applying the partial vacuum.

The principle of the present invention can be applied in non-medical fields where it may be desirable to temporarily and reversibly immobilize a body component or a whole body for reasons of comfort or safety. For example, it can be used by sufferers of arthritis to find a comfortable position for sleeping or other activities. For example, it can be used by operators of equipment (automobiles, airplanes, trucks) to form a protective environment for regions of the body (head, shoulders, legs) for safety purposes.

As can be appreciated, the lowering of the pressure to lock the cast or brace cushion may be done manually by a hand pump, or by computer control using a mouse or voice control.

A number of variations and modifications of the inventions can be used. As will be appreciated, it would be possible to provide for some features of the inventions without providing others.

The present invention, in various embodiments, includes components, methods, processes, systems and/or apparatus substantially as depicted and described herein, including various embodiments, sub-combinations, and subsets thereof. Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, for example for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A medical device, comprising:
   an instrument surface;
   an eyepiece engaging and locating a patient's eye relative to the instrument surface; and
   at least one face rest, the face rest comprising a base plate and a cushion member having a surface to engage a non-planar body part of the patient for at least one of imaging and treatment, wherein, in a first mode, no vacuum is imparted to the cushion member and, in a second mode, a vacuum is imparted to the cushion member.

2. The medical device of claim 1, wherein an interior of the cushion member comprises a granular material, wherein, in the first mode, the interior of the cushion member is at a first pressure, wherein, in the second mode, the interior of the cushion member is at a second pressure, and wherein the first pressure is greater than the second pressure.

3. The medical device of claim 1, wherein the at least one of treating and imaging is imaging, wherein the non-planar body part is a patient's face, and wherein the medical device images the patient's eye.

4. The medical device of claim 1, wherein the cushion member surface is disposable.

5. The medical device of claim 1, wherein the base plate supporting the surface is movable relative to the instrument surface to be repositionable to accommodate the body part.

6. The medical device of claim 5, wherein the base plate is magnetically attracted to the instrument surface.

7. The medical device of claim 1, wherein a user may select between the first mode and the second mode with a single hand.

8. A medical device comprising:
   and instrument surface; an eyepiece engaging and locating a patient's eye relative to the instrument surface; and a cushion member operable to engage a body part of a patient for at least one of imaging and treatment and operable to fix a patient's eye relative to the instrument surface, wherein, in a first mode, the cushion member is moveable relative to the instrument surface, is under a first pressure and is deformable and wherein, in a second mode, the cushion member is not moveable relative to the instrument surface, is under a second pressure and is rigid, wherein the second pressure is less than the first pressure.

9. The medical device of claim 8, wherein the cushion member comprises a granular material configured to operate in a first state that is deformable and a second state that is rigid.

10. A medical device, comprising:
    an instrument surface;
    an eyepiece engaging and locating a patient's eye relative to the instrument surface; and
    at least one face rest, the face rest comprising a base plate and a cushion member having a surface to engage a non-planar body part of the patient for at least one of imaging and treatment, wherein, in a first configuration, the base plate is movable relative to the instrument surface to be repositionable and the cushion member is deformable and, in a second configuration, the base plate is not movable relative to the instrument surface to be repositionable and the cushion member is rigid.

11. The medical device of claim 10, wherein a user may select between the first configuration and the second configuration with a single hand.

* * * * *